United States Patent [19]
// Goldschmidt et al.

[11] Patent Number: 5,832,973
[45] Date of Patent: Nov. 10, 1998

[54] SANITARY CARBON CHARGING SYSTEM

[75] Inventors: Norman Goldschmidt, Syracuse; Kenton Shultis, Manlius; Gary V. Faigle, Chittenango, all of N.Y.; Connie Esenther, Andover, Mass.

[73] Assignee: Bristol-Myers Squibb Company, New York, N.Y.

[21] Appl. No.: 950,806

[22] Filed: Oct. 14, 1997

[51] Int. Cl.$^6$ ........................................... B65B 1/06
[52] U.S. Cl. ..................... 141/383; 141/94; 141/67; 141/89; 141/364; 73/324; 222/108; 222/156; 222/460
[58] Field of Search ................ 73/323, 324; 141/67, 141/89, 91, 92, 94, 363, 364, 383, 11

[56] References Cited

U.S. PATENT DOCUMENTS

| | | |
|---|---|---|
| 3,190,509 | 6/1965 | Kirchhoefer . |
| 3,232,494 | 2/1966 | Poarch . |
| 3,347,741 | 10/1967 | Hutchison . |
| 3,365,240 | 1/1968 | Gordon . |
| 3,455,490 | 7/1969 | Jolley . |
| 3,650,436 | 3/1972 | Barber . |
| 3,915,347 | 10/1975 | Biggart . |
| 3,998,686 | 12/1976 | Meiling et al. . |
| 4,085,521 | 4/1978 | Neuroth ........................ 34/89 |
| 4,299,338 | 11/1981 | Jain et al. . |
| 4,381,067 | 4/1983 | Catelli . |
| 4,623,516 | 11/1986 | Weiler et al. . |
| 4,753,375 | 6/1988 | Takei et al. . |
| 4,912,681 | 3/1990 | Halsey et al. . |
| 4,957,133 | 9/1990 | Linz et al. . |

Primary Examiner—David J. Walczak
Assistant Examiner—Lynette C. Goodwin
Attorney, Agent, or Firm—Morton S. Simon

[57] ABSTRACT

Apparatus is provided for charging a bioreactor with feed material through a sight port in the bioreactor vessel wall without compromising sterility of the material or the vessel or releasing organisms from the vessel to the surrounding atmosphere.

20 Claims, 2 Drawing Sheets

SANITARY CARBON CHARGING SYSTEM

FIELD OF INVENTION

The present invention relates generally to bioreactor vessels and, more particularly, to apparatus and method for charging a bioreactor vessel during operation with dry, flowable material without compromising the sterility of either the material or the bioreactor vessel, or releasing organisms from the bioreactor vessel to the surrounding atmosphere.

BACKGROUND OF THE INVENTION

During the operation of bioreactor vessels, it is commonly necessary to charge the bioreactor vessel with material. Depending on the material being introduced and/or processed within the bioreactor vessel, various apparatus and methods have been developed for charging bioreactor vessels.

When innocuous material is being introduced and processed within the bioreactor vessel and there is no concern for the release of hazardous material to the surrounding atmosphere or the introduction of extraneous materials from the surrounding atmosphere into the vessel, the bioreactor vessel is typically charged by removing a detachable sight glass assembly from the vessel and pouring the material through the sight glass port and into the vessel. Existing sight glass assemblies generally consist of a hollow tube which is removably coupled at one end to the sight glass port and includes a sight glass attached at the other end.

Conventional sight glass assemblies may further include a source of pressurized steam coupled in flow communication with the interior of the sight glass assembly to facilitate the removal of residual material which may obstruct the view through the sight glass and into the vessel. Accordingly, pressurized steam may be injected into the sight glass assembly to clear any residual material from within the sight glass assembly or on the interior surface of the sight glass. Since the interior of the sight glass assembly is in flow communication with the interior of the bioreactor vessel, any pressurized steam injected into or residual material removed from the sight glass assembly will condense and accumulate in the bioreactor vessel. However, the introduction of such condensate may compromise the desired reaction in the bioreactor vessel.

Alternatively, when it is desired to maintain a sterile environment within the bioreactor vessel and/or protect against the release of hazardous material from the bioreactor vessel to the surrounding atmosphere, significantly more complicated apparatus and methods for charging the vessel have been developed. In order to provide for sterile charging of feed material, conventional bioreactors are typically coupled by a fixed piping system to a second bioreactor vessel. The piping system includes a normally closed shut-off valve at each end where it is coupled to the bioreactor vessel and the second vessel. The piping system is also coupled to a pressurized steam source for sterilizing the interior of the piping system extending between the bioreactor vessel and the second vessel.

According to above-described prior art apparatus, sterile charging is affected by closing the shutoff valves coupling the piping system to the bioreactor vessel and the second vessel. Placing charging feed into the second vessel. Sterilizing the charging feed and the piping system by heating the second vessel and steaming the piping system. Finally, a large volume of pressurized gas, typically nitrogen gas, is injected into the second vessel and the shutoff valves are opened, such that the charging material is forced from the second vessel, through the piping conduit and into the bioreactor vessel.

However, there are several problems with the prior art apparatus and method for sterilized charging of bioreactor vessels. For example, after the piping system is steamed a residual amount of moisture will inevitably remain within the piping system. When transferring dry charging material, such as fine carbon feed, from the second vessel to the bioreactor vessel, an undetermined portion of the charging material will absorb this moisture and remain within the piping system, thereby affecting the accuracy of the composition of material within the bioreactor vessel. This loss of charging material is a particular problem when charging the bioreactor vessel with small quantities of material, whereby even the slightest variance in the quantity of material introduced in the bioreactor vessel may significantly affect the intended reaction. In addition, the use of large quantities of pressurized gas to force the charging material from the second vessel to the bioreactor vessel causes unwanted turbulence within the bioreactor vessel which may also affect the desired reaction therein. These and other difficulties with the prior art apparatus and methods have been obviated in a novel manner by the present invention.

It is, therefore, a principal object of the present invention to provide an apparatus and method for charging a bioreactor vessel, during operation with dry flowable material, without compromising the desired reaction therein.

It is a further object of the present invention to provide an apparatus and method for the sterilized charging of a bioreactor vessel without loss of charging material.

It is a further object of the present invention to provide an apparatus and method for the sterilized charging of a bioreactor vessel without causing unwanted turbulence within the bioreactor vessel.

It is still a further object of the present invention to provide an apparatus and method for removing residual material, which may obstruct the view through the sight glass and into the bioreactor vessel, without introducing extraneous materials into the bioreactor vessel.

Objects and advantages of the invention are set forth in part above and in part below. In addition, these and other objects and advantages of the invention will become apparent herefrom, or may be appreciated by practice with the invention, the same being realized and attained by means of instrumentalities, combinations and methods pointed out in the appended claims. Accordingly, the present invention resides in the novel parts, constructions, arrangements, improvements, methods and steps herein shown and described.

SUMMARY OF THE INVENTION

The present invention provides an apparatus and method for sterile charging of bioreactor vessels with feed material. In general, the present invention comprises a specialized sight glass assembly which may be coupled to either (1) a conventional sight glass attachment during normal operation of the bioreactor vessel or (2) a canister attachment for charging the bioreactor vessel with feed material. The specialized sight glass assembly includes a sanitary valve, which when closed provides a steamable and bubble tight seal. When the sight glass assembly is coupled to the sight glass attachment, the sanitary valve may be closed to provide a sealed chamber within the upper portion of the sight glass assembly to facilitate sterilized cleaning of the sight glass. In addition, when the sight glass assembly is coupled to the canister attachment, the invention provides for sterilized charging of the bioreactor vessel with feed material. Further features and advantages of the present invention are provided in the following description of the preferred, but not exclusive, embodiment which is given by example and is in no way restrictive of the scope of the present invention.

DESCRIPTION OF THE PREFERRED EMBODIMENTS

Figure 1:
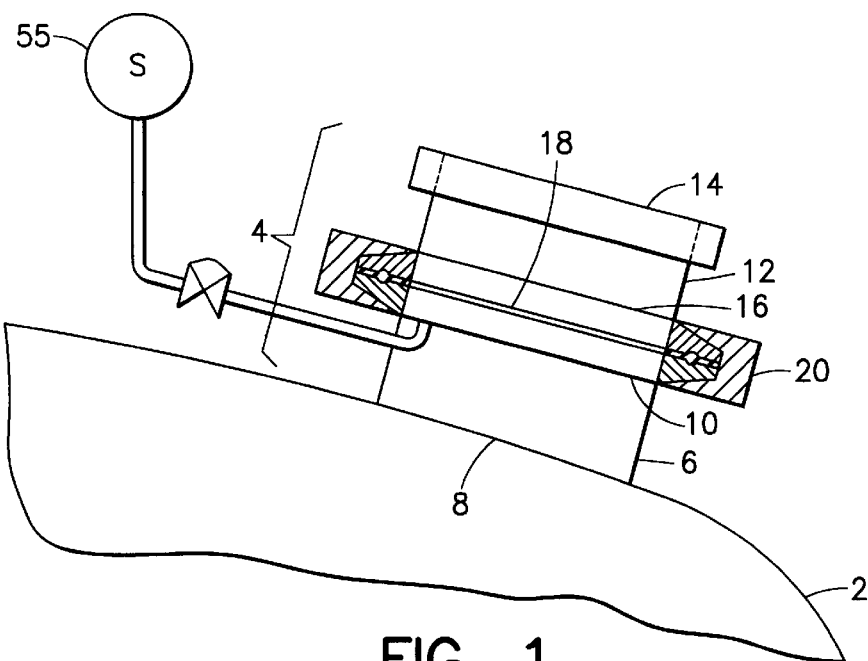
FIG. 1 is a perspective view, with partial cutaway, of a bioreactor vessel to which the present invention may be applied.
Figure 2:
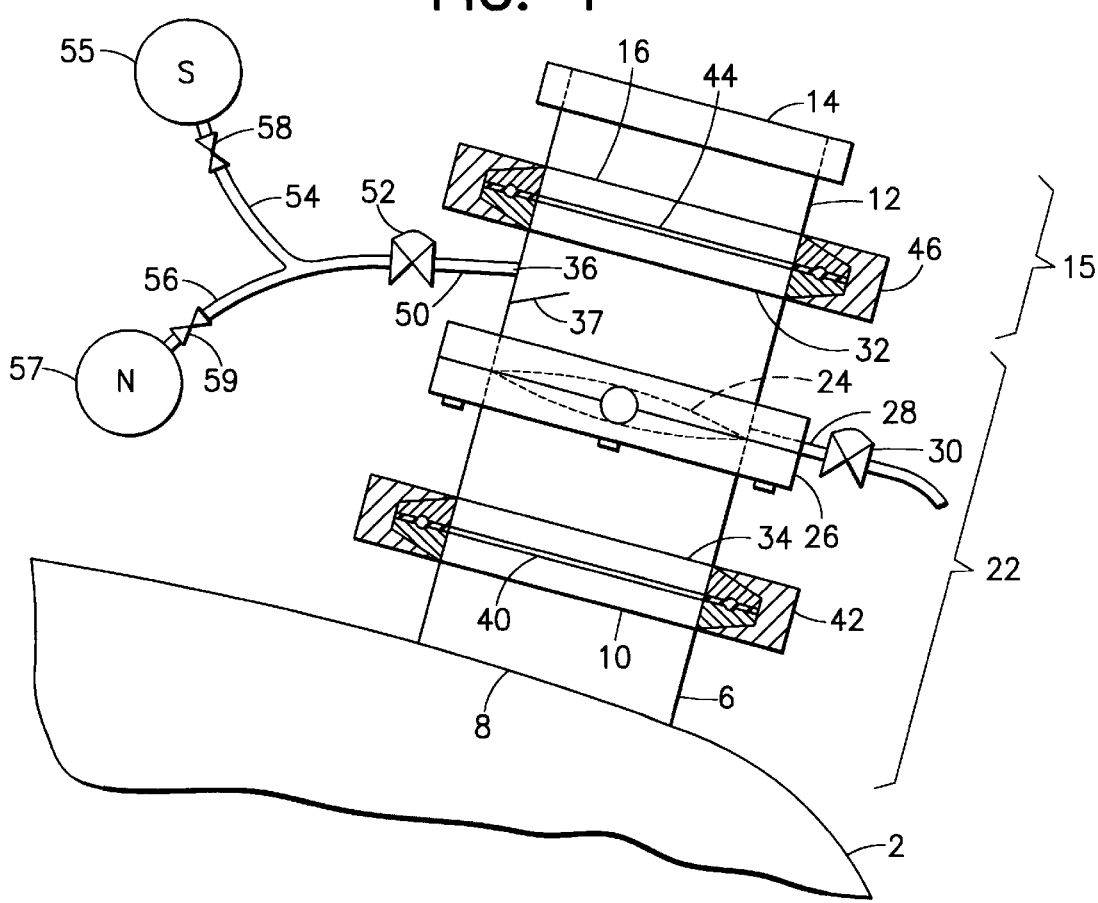
FIG. 2 is a perspective view, with partial cutaway, of an embodiment of the present invention incorporating a removable cover/sight glass attachment.
Figure 3:
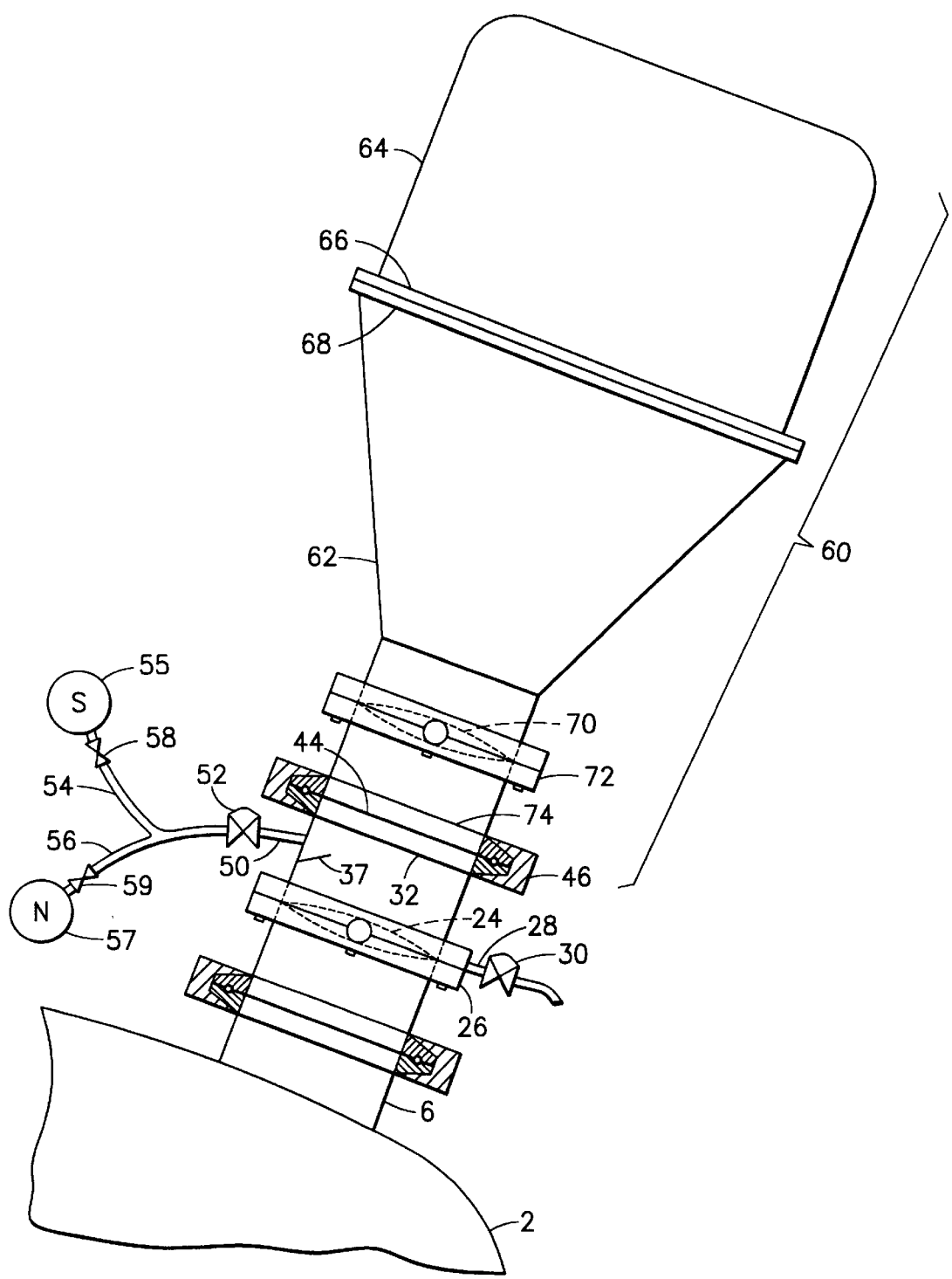
FIG. 3 is a perspective view, with partial cutaway, of an embodiment of the present invention incorporating a removable canister attachment.

Referring generally to the embodiments of the invention shown in the accompanying drawings, wherein like reference numbers refer to like parts throughout the various views, the basic principles of the broadest aspects of the invention can be appreciated from FIGS. 1–3.

As shown in FIG. 1, a conventional bioreactor vessel typically includes an electrically grounded tank 2 having a standard 4 inch triclover sight port assembly 4. The sight port assembly 4 generally includes a rigid hollow tube 6 mounted at its base end to the outside surface of the tank such that it is centrally disposed over port 8. Tube 6 also includes a ferrule 10 mounted at its opposite end. The removable sight glass includes a rigid hollow tube 12 having a fused sanitary sight glass 14 mounted at its top end and a ferrule 16 mounted at its base end. The base end of removable sight glass and the opposite end of tube 6 are attached by sealingly coupling ferrules 16 and 10 via a gasket 18 and clamp 20. As further illustrated in FIG. 1, when the sight glass assembly is coupled to the bioreactor tank 2, the longitudinal axis of tubes 6 and 12 are inclined at a fixed angle relative to the vertical axis of bioreactor tank 2.

During normal operation of the bioreactor vessel, the present invention is in the general state of assembly illustrated in FIG. 2, whereby the conventional sight port assembly 4 described above with reference to FIG. 1 is modified to include an extension tube 22 coupled between tube 6 and removable sight glass tube 12. Extension tube 22 includes a sanitary butterfly valve 24 which is coupled to extension tube 22 by a one-piece seat 26. Seat 26 and butterfly valve 24 act together to provide an elastomeric, bubble tight and steamable seal when butterfly valve 24 is in a closed position. To this end, butterfly valve 24 and seat 26 are preferably made of a platinum-cured silicon material which functions to provide a bubble tight seal under conditions exceeding 121° C. and 35 PSI. The butterfly valve 24 and seat 26 are modified to have an outlet coupled to a ¼ inch condensate drain tube 28. Condensate drain tube 28 includes a condensate valve 30 which functions to regulate the flow of liquid or gas from within extension tube 22 through condensate drain tube 28. Condensate valve 30 is preferably a diaphragm valve. Extension tube 22 also includes ferrules 32 and 34 mounted at each of its top end and bottom end, respectively.

As shown in FIG. 2, ferrule 34 at the bottom end of extension tube 22 is sealingly coupled with ferrule 10 at the top end of tube 6 via gasket 40 and clamp 42. Similarly, ferrule 32 at the top end of extension tube 22 is sealingly coupled with ferrule 16 at the base end of removable sight glass tube 12 via gasket 44 and clamp 46.

As further shown in FIG. 2, extension tube 22 includes a port 36 extending transversely through the wall of the extension tube at a position between butterfly valve 24 and ferrule 32. Tube 50 is coupled at its first end to port 36 and is coupled at its second end to conduits 54 and 56 which lead to steam source 55 and nitrogen source 57, respectively. Conduits 54 and 56 are equipped with shut-off valves 58 and 59, for regulating the supply of either steam or nitrogen from their respective sources. Tube 50 also includes a valve 52 positioned between its first end and second end which functions to regulate the flow of either steam or nitrogen through tube 50. Valve 52 is preferably a diaphragm valve.

As illustrated in FIG. 3, the assembly shown in FIG. 2 can be adapted to include a canister attachment when it is desired to charge the bioreactor tank 2 with feed material. To this end, the sight glass attachment shown in FIG. 2 is removed and replaced with a canister attachment (generally referred to as 60).

As shown in FIG. 3, the canister attachment comprises a removable funnel 62 and a canister 64. Canister 64 has an opening 66 which couples to the top end of funnel 68 by means of quick-release attachment band. Funnel 62 includes a sanitary butterfly valve 70 which is coupled to the funnel by means of a one-piece seat 72. Seat 72 and butterfly valve 70 act together to provide an elastomeric, bubble tight and steamable seal when butterfly valve 70 is in a closed position. To this end, butterfly valve 70 and seat 72 are preferably made of a platinum-cured silicon material which functions to provide a bubble tight seal under conditions exceeding 121° C. and 35 PSI. Funnel 62 also includes a ferrule 74 mounted at the base of its bottom end. When charging the bioreactor vessel, the canister attachment 60 is connected to the sight port assembly by sealingly coupling ferrule 74 at the bottom end of funnel 62 to ferrule 32 at the top end of extension tube 22 via a gasket 44 and clamp 46.

As previously stated, during normal operation of the bioreactor vessel the present invention is in the state of assembly illustrated in FIG. 2. While in this state of assembly, butterfly valve 24 is in a normally open position to permit viewing of the inside of the reactor vessel through sight glass 14. To enhance such viewing, the present invention provides a method for blowing clean sight glass 14 without introducing extraneous and/or contaminating materials into the bioreactor vessel. To this end, butterfly valve 24 is closed such that a steamable and bubble tight sealed chamber is provided in the upper portion of the sight glass assembly. Next, valves 58 and 52 are opened such that steam is injected into the sealed chamber, thereby clearing any residual material from the interior surface of sight glass 14. Valve 58 is then closed and valve 59 is opened such that nitrogen gas is introduced into the sealed chamber, thereby cooling the steam and forming a condensate comprising the residual material. Valves 52 and 59 are closed and condensate valve 30 is opened, such that any condensate formed within the sealed chamber will accumulate on the top surface of butterfly valve 24 and drain through condensate tube 28. It will be appreciated that due to the combination of the inclined angle of the sight glass assembly and the elliptical surface of butterfly valve 24, a single lowest point will be defined within the sealed chamber at a position adjacent to the inlet of condensate tube 28. Moreover, it will be appreciated that the removal of condensate from within extension tube 22 may be further affected by introducing addition nitrogen gas to pressurize the interior chamber of extension tube 22, such that any residual condensate which might otherwise remain in extension tube 22 will be forced through condensate tube 28.

To further facilitate the cleaning of residual material from sight glass 14, extension tube 22 may further include a deflector plate 37 located immediately below port 36. As shown in FIGS. 2 and 3, deflector plate 37 is configured such that the gas entering through port 36 is more specifically directed toward sight glass 14.

When it is desired to charge the bioreactor tank, butterfly valve 24 is closed such that it forms a steamable and bubble tight seal with seat 26. Then steam valve 58, valve 52, and condensate valve 30 are opened whereby steam will pass from source 55, through conduit 54 and tube 50, and into the upper portion of extension tube 22 defined by the space between sight glass 14 and butterfly valve 24. After the steam has sterilized and inactivated the atmosphere occupying this space, steam valve 58 is closed and nitrogen valve 59 is opened. Nitrogen then passes from source 57, through conduit 56 and tube 50, and into the upper portion of the extension tube 22, and thereby cools the atmosphere occupying this space causing the steam to condense. The condensate accumulates on the top of butterfly valve 24 before it passes through the condensate drain tube 28. After the upper portion of the extension tube 22 is sufficiently cooled and the condensate has been purged through condensate drain tube 28, nitrogen valve 59, valve 52 and condensate valve 30 are closed. Clamp 46 is then opened and sight glass attachment 15 is removed.

Next, canister 64 is filled with charging material and assembled with funnel 62. This assembly is then sterilized in a dry heat oven. It should be noted that while the canister assembly is being sterilized in the dry heat oven, the canister must be allowed to breath. To this end, butterfly valve 70 is opened and a HEPA filter is attached to the small end of funnel 62. After the canister attachment has been sterilized, butterfly valve 70 is closed and the HEPA filter is removed. The canister attachment is then sealingly coupled to the top end of the extension tube 22 by fitting gasket 44 between the abutting surfaces of ferrules 74 and 32, and closing clamp 46 about the outside edges of ferrules 74 and 32.

In order to sterilize the atmosphere occupying the space between butterfly valves 70 and 24 of the assembly shown in FIG. 3, steam valve 58, valve 52 and condensate valve 30 are opened such that steam passes from source 55, through conduit 54 and tube 50, and into this space. After the steam has sterilized the atmosphere occupying this space, steam valve 58 is closed and nitrogen valve 59 is opened. Nitrogen gas then passes from source 57, through conduit 56 and tube 50, and into extension tube 22, thereby cooling this space and causing the steam to condense. The condensate accumulates on the top of butterfly valve 24 before it passes through the condensate drain tube 28. After this area is sufficiently cooled and the condensate has been discharged through condensate drain tube 28, nitrogen valve 59, valve 52 and condensate valve 30 are closed.

Next butterfly valves 24 and 70 are opened such that the charging material in canister 64 falls under the force of gravity through funnel 62, extension tube 22 and tube 6, and into bioreactor tank 2. After essentially all of the charging material has entered bioreactor tank 2, canister 64 is blown clean of any remaining material. To this end, nitrogen valve 59 and valve 52 are opened, permitting nitrogen gas to flow from source 57, through conduit 56, tube 50 and extension tube 22, and into canister 64. After the canister is emptied of any remaining material, nitrogen valve 59 and valve 52 are closed.

After charging of the bioreactor tank is completed, butterfly valves 24 and 70 are closed. In the same manner described above with reference to FIG. 3, the atmosphere occupying the space enclosed within butterfly valves 24 and 70 is sterilized and deactivated by injecting steam and subsequently nitrogen gas into this space.

The assembly of the present invention is then returned to its normal state by removing canister attachment 60 and coupling sight glass attachment 15 to the top end of extension tube 22. As previously described with reference to FIG. 2, the atmosphere occupying the space between sight glass 14 and butterfly valve 24 is sterilized by injecting steam and then nitrogen gas into this space. Finally, butterfly valve 24 is returned to its normally open position so that the inside of bioreactor tank 2 can be viewed through sight glass 14.

While only a few embodiments have been illustrated and described in connection with the present invention, various modifications and changes in both the apparatus and method will become apparent to those skilled in the art. All such modifications or changes falling within the scope of the claims are intended to be included therein.

We claim:

1. An apparatus for charging a bioreactor vessel with feed material through a sight port in the bioreactor vessel wall, comprising:

a) a tube having a base end coupled to the bioreactor vessel wall at a position centrally disposed over the sight port and having a top end extending outward from the surface of the bioreactor vessel wall;

b) a first valve operatively associated with the tube, which when in a normally-open position permits flow communication between an upper portion of the interior of the tube and the bioreactor vessel and when in a closed position prohibits flow communication between the upper portion of the interior of the tube and the bioreactor vessel;

c) a conduit having an inlet end coupled in flow communication with the interior of the tube at a position between an upper surface of the first valve and the top end of the tube;

d) flow enabling means for permitting, when desired, flow of fluids from the interior of the tube through the inlet end of the conduit;

e) a first source of pressurized gas coupled in flow communication with the interior of the tube at a position above the upper surface of the first valve;

f) flow enabling means for permitting, when desired, the flow of pressurized gas from the first source of pressurized gas to the interior of the tube;

g) a second source of pressurized gas coupled in flow communication with the interior of the tube at a position above the upper surface of the first valve;

h) flow enabling means for permitting, when desired, the flow of pressurized gas from the second source of pressurized gas to the interior of the tube; and i) a chamber having a bottom end removably coupled to the top end of the tube, such that the interior of the chamber is in flow communication with the interior of the tube.

2. The apparatus according to claim 1, wherein the chamber comprises a sight glass attachment adapted for viewing the interior of the bioreactor vessel through the sight port in the bioreactor vessel wall.

3. The apparatus according to claim 1, wherein the chamber comprises a canister attachment adapted for sterilized charging of the bioreactor vessel with feed material.

4. The apparatus according to claim 3, wherein the canister attachment comprises:
   a) a container having a bottom end coupled in flow communication with the top end of the tube;
   b) a second valve operatively associated with the container, which when in a normally-closed position prohibits flow communication between an upper portion of the interior of the container and the interior of the tube and when in an open position permits flow communication between the interior of the container and the interior of the tube.

5. The apparatus according to claim 4, wherein the second valve is coupled to the container by a one-piece valve seat.

6. The apparatus according to claim 5, wherein the second valve and the valve seat function to provide an elastomeric, bubble tight and steamable seal between the upper portion of the interior of the container and the interior of the tube when the second valve is in the normally-closed position.

7. The apparatus according to claim 6, wherein the second valve and the valve seat comprise a platinum-cured silicon material.

8. The apparatus according to claim 7, wherein the second valve comprises a butterfly valve.

9. The apparatus according to claim 8, wherein the container comprises:
   a) a removable funnel having an open top end and an open bottom end, and
   b) a canister coupled in flow communication with the top end of the funnel.

10. The apparatus according to claim 1, wherein the inlet end of the conduit is coupled in flow communication with the interior of the tube at substantially the lowest point within the upper portion of the interior of the tube when the first valve is in the closed position.

11. The apparatus according to claim 10, wherein the first valve is coupled to the tube by a one-piece valve seat.

12. The apparatus according to claim 11, wherein the first valve and the valve seat function to provide an elastomeric, bubble tight and steamable seal between the upper portion of the interior of the tube and the bioreactor vessel when the first valve is in the closed position.

13. The apparatus according to claim 12, wherein the first valve and the valve seat comprise a platinum-cured silicon material.

14. The apparatus according to claim 13, wherein the first valve comprises a butterfly valve.

15. The apparatus according to claim 1, wherein the first source of pressurized gas is steam.

16. The apparatus according to claim 1, wherein the second source of pressurized gas is nitrogen.

17. The apparatus according to claim 1, which further includes a deflector plate coupled to the interior surface of the tube and which is configured to direct gas flowing from the first source of pressurized gas and/or the second source of pressurized gas toward the top end of the tube.

18. The apparatus according to claim 1 wherein the flow enabling means for permitting flow of fluids from the interior of the tube through the inlet end of the conduit is a diaphragm valve.

19. A method for charging a bioreactor vessel with feed material through a sight glass assembly coupled to a sight port in the bioreactor vessel wall, wherein the sight glass assembly comprises a tube having a bottom end in flow communication with the bioreactor vessel and a top end extending outward from the bioreactor vessel, a first valve operatively associated with the tube, a sight glass attachment coupled to a top end of the tube, and an alternative canister attachment comprising a container having a bottom end and a second valve operatively associated with the container, comprising the steps of:
   a) closing the first valve to provide a generally sealed chamber within the top portion of the sight port assembly;
   b) sterilizing the chamber within the top portion of the sight port assembly;
   c) removing the sight glass attachment from the top end of the tube;
   d) placing feed material into the canister attachment and sterilizing the feed material;
   e) closing the second valve to provide a generally sealed chamber in the top portion within the canister attachment;
   e) coupling the bottom end of the canister attachment to the top end of the tube;
   f) sterilizing the chamber between the first valve and the second valve;
   g) opening the first valve and the second valve such that the feed material in the canister attachment falls under the force of gravity through the tube and into the bioreactor vessel;
   h) closing the first valve and sterilizing the chamber above the first valve;
   i) removing the canister attachment from the top end of the tube; and
   j) coupling the sight glass attachment to the top end of the tube.

20. The method according to claim 19, which further comprises removing any condensate from within the chamber between the first valve and the second valve which may be formed when sterilizing the chamber.

* * * * *